United States Patent [19]

Warriner

[11] Patent Number: Plant 7,473

[45] Date of Patent: Mar. 19, 1991

[54] ROSE PLANT JACTER

[75] Inventor: William A. Warriner, Tustin, Calif.

[73] Assignee: Bear Creek Gardens, Inc., Medford, Oreg.

[21] Appl. No.: 478,192

[22] Filed: Feb. 9, 1990

[51] Int. Cl.[5] ..... A01H 5/00

[52] U.S. Cl. ..... Plt./20

[58] Field of Search ..... Plt./20

*Primary Examiner*—James R. Feyrer

*Attorney, Agent, or Firm*—Klarquist, Sparkman, Campbell, Leigh & Whinston

[57] ABSTRACT

A hybrid tea rose variety having bright red flowers borne on strong peduncles, seven (7) leaflet leaves, presence of red pigment in peduncles, and vigorous upright growth and dark green glossy leaves.

1 Drawing Sheet

This present invention relates to a new and distinct variety of rose plant named JACTER of the hybrid tea class which was originated by me by crossing the variety Showstopper, U.S. Plant Pat. No. 4,581, with an unnamed seedling.

The primary objective of this breeding was to produce a new rose variety having the bright red flower color of Showstopper, but without Showstopper's weak neck. The objective was substantially achieved along with other desirable improvements as evidenced by the following unique combination of characteristics which are outstanding in the new variety and which distinguish it from its parents as well as from all other varieties of which I am aware:

1. Bright clear red flowers borne on strong peduncles.
2. Seven (7) leaflet leaves.
3. Presence of red pigment in peduncles.
4. Vigorous upright growth and dark green glossy leaves.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where oridinary dictionary significance of color is indicated.

Parentage:

*Seed parent.*—Showstopper, U.S. Plant Pat. No. 4,851.

*Pollen parent.*—An unnamed seedling.

Classification:

*Botanical.*—Rosa hybrida.

*Commercial.*—Hybrid tea.

FLOWER

Observations made from specimens grown in a garden is Somis, Calif. from June to October, 1989.

Blooming habit: Recurrent.

Bud:

*Size.*—1½ inch when the petals start to unfurl.

*Form.*—Short, pointed ovoid.

*Color.*—When sepals first divide: Red Group 44A. When half blown: The upper sides of the petals are Red Group 44A; and the lower sides of the petals are Red Group 44A.

*Sepals.*—Color: Grey green. Surface texture: Covered in fine hairs. Three normally to heavily appendaged sepals and two unappendaged sepals with hairy edges.

*Receptacle.*—Color: Medium green with a red blush. Shape: Funnel. Size: Medium. Surface: Smooth.

*Peduncle.*—Length: Medium. Surface: Smooth. Color: Bronzy. Strength: Stiff, erect.

Bloom:

*Size.*—Large. Average open size is 5 inches.

*Borne.*—Singly.

*Stems.*—Long, strong.

*Form.*—When first open: High centered. Permanence: Retains its form to the end, outer petals curl back, quill fashion.

*Petalage.*—Number of petals under normal conditions: 30.

*Color.*—Upper side of petals is: Red Group 44A. Reverse side of petals is: Red group 44A. Base of petals is: Small yellow half moon at the point of attachment. Major color on the upper side is: Red Group 44A.

*Variegations.*—Occasional white streak on a guard petal on a petaloid.

*Discoloration.*—General tonality at end of first day: No change; at the end of the third day: No change.

*Fragrance.*—Slight.

Petals:

*Texture.*—Thick.

*Shape.*—Deltoid.

*Form.*—Tips slightly recurved, edges slightly quilled.

*Arrangement.*—Imbricated.

*Persistence.*—Drop off cleanly.

*Lastingness.*—On the plant: Very long. As a cut flower: Very long.

Reproductive parts:

*Anthers.*—Size: Medium. Color: Yellow. Arrangement: Regular around styles.

*Filaments.*—Color: White.

*Pollen.*—Color: Gold yellow.

*Styles.*—Color: Red.
*Stigmas.*—Color: Greenish white.
Form: Bush.
Growth: Vigorous, upright.
Foliage:
*Number of leaflets on normal mid-stem leaves.*—5 or 7.
*Size.*—Large.
*Quantity.*—Normal.
*Color.*—New foliage: Red. Old foliage. Glossy dark green.
Leaflets:
*Shape.*—Pointed oval.
*Texture.*—Leathery, glossy.
*Edge.*—Serrated.
*Serration.*—Single, small.
*Petiole.*—Rachis: Green. Underside: Rough, with prickles.
*Stipules.*—Short, bearded.
*Disease resistance.*—Susceptible to mildew under normal growing conditions at Somis, Calif.

Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Hooked slightly downward.
*Color when young.*—Red.
Small Prickles:
*Quantity.*—On main stalks: None. On laterals: None.

I claim:

1. A new and distinct variety of rose plant of the hybrid tea class, substantially as herein shown and described, characterized particularly as to novelty by bright red, high centered flowers born on strong peduncles, dark green glossy foliage, strong upright habit of growth, presence of red pigment in the peduncles and many seven (7) leaflet leaves.

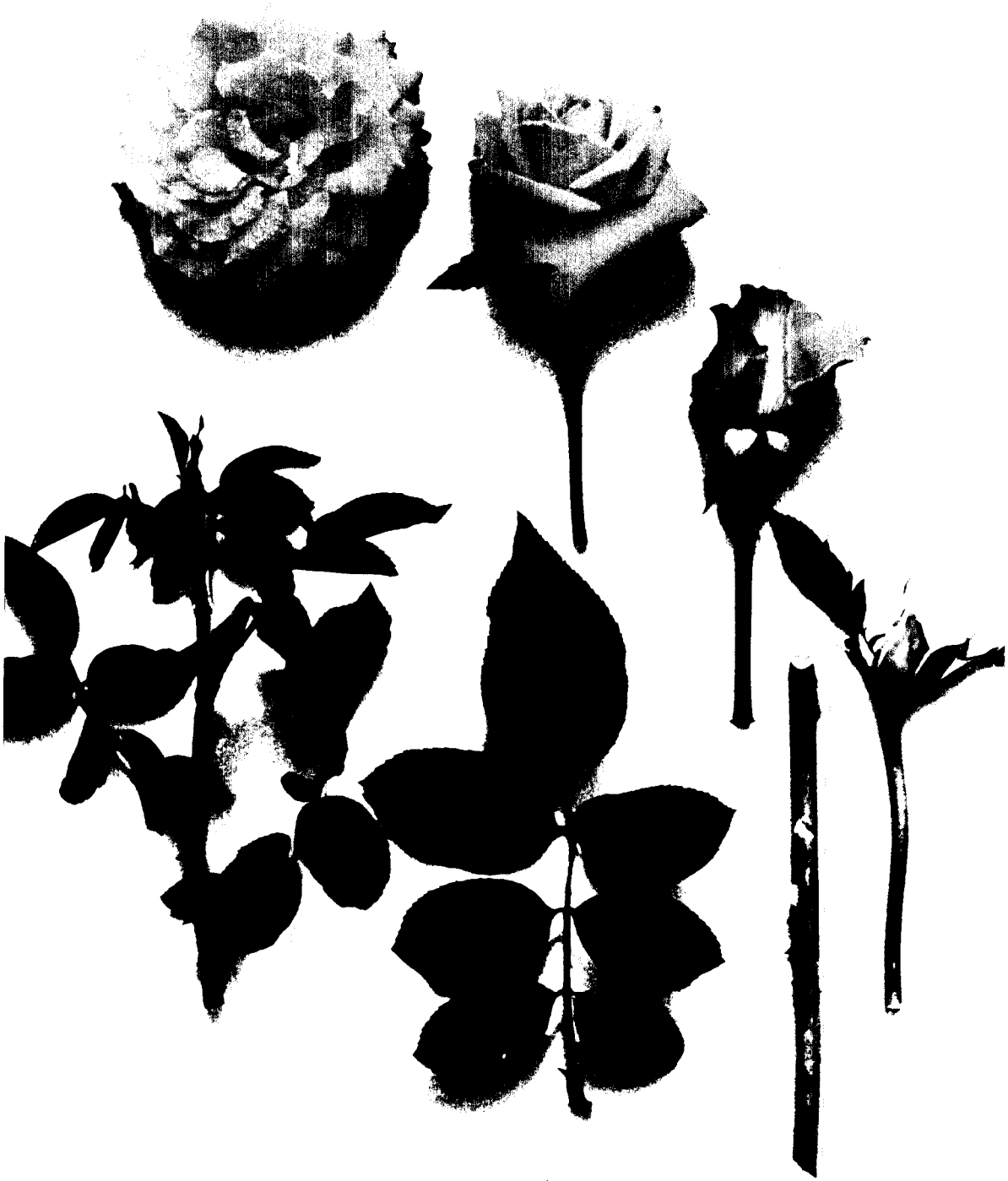

* * * * *